United States Patent
Prestipino

(10) Patent No.: US 7,018,207 B2
(45) Date of Patent: Mar. 28, 2006

(54) DENTAL IMPLANT ANALOG HAVING RETENTION GROOVE FOR SOFT TISSUE MODELING

(75) Inventor: David M. Prestipino, Star Tannery, VA (US)

(73) Assignee: Implant Innovations, Inc., Palm Beach, FL (US)

( * ) Notice: Subject to any disclaimer, the term of this patent is extended or adjusted under 35 U.S.C. 154(b) by 290 days.

(21) Appl. No.: 10/081,422

(22) Filed: Feb. 22, 2002

(65) Prior Publication Data

US 2003/0162148 A1    Aug. 28, 2003

(51) Int. Cl.
*A61C 9/00* (2006.01)

(52) U.S. Cl. .................... 433/213; 433/214

(58) Field of Classification Search .............. 733/173, 733/174, 213, 214
See application file for complete search history.

(56) References Cited

U.S. PATENT DOCUMENTS

| | | | |
|---|---|---|---|
| 4,850,870 A | 7/1989 | Lazzara et al. | 433/174 |
| 4,854,872 A * | 8/1989 | Detsch | 433/173 |
| 4,955,811 A | 9/1990 | Lazzara et al. | 433/173 |
| 5,312,256 A * | 5/1994 | Scortecci | 433/174 |
| 5,419,702 A | 5/1995 | Beaty et al. | 433/214 |
| 5,476,383 A | 12/1995 | Beaty et al. | 433/214 |
| 5,674,071 A | 10/1997 | Beaty et al. | 433/172 |
| 5,762,500 A * | 6/1998 | Lazarof | 433/213 |
| 5,863,201 A * | 1/1999 | Lazzara et al. | 433/201.1 |
| 5,871,358 A * | 2/1999 | Ingber et al. | 433/213 |
| RE36,126 E | 3/1999 | Beaty et al. | 433/214 |
| 5,904,483 A * | 5/1999 | Wade | 433/173 |
| 5,934,906 A * | 8/1999 | Phimmasone | 433/172 |
| RE36,689 E | 5/2000 | Beaty et al. | 433/214 |
| 6,217,331 B1 | 4/2001 | Rogers et al. | 433/173 |
| 6,332,777 B1 * | 12/2001 | Sutter | 433/173 |
| 6,540,514 B1 * | 4/2003 | Falk et al. | 433/173 |
| 6,672,871 B1 * | 1/2004 | Hurson | 433/172 |

OTHER PUBLICATIONS

Bicon Dental Implants, Catalogue And Procedure Manual, 7 pages (1995).
Calcitek, Inc., Price List & Ordering Information, 60 pages (Jul. 1991).
Dentsply/Implant Division, Product Catalog, 21 pages (1992).
Friatec, Price List, 40 pages (Oct. 1998).
Impla-Med, Inc., Product Catalog, 44 pages (1995).
Implant Innovations, Catalog, 62 pages (Jul. 1990).
Implant Support Systems, Inc., Catalog, 42 pages (Summer 1993).
IMTEC Corporation, Catalog & Owners Manual, 4th Edition, 20 pages (Feb. 1994).
Minimatic Implant Systems, Product Catalog, 40 pages (May 15, 1994).
Steri-Oss, Inc., Abutment Selection Guide, 36 pages (Jun. 1994).
Stryker Dental Implants, Price List, 46 pages (Apr. 1993).

* cited by examiner

*Primary Examiner*—Ralph A. Lewis
(74) *Attorney, Agent, or Firm*—Jenkens & Gilchrist

(57) ABSTRACT

An implant analog is for supporting an article that is used to develop a dental prosthesis. The analog provides a main body for being anchored in a model of a mouth of a patient. The main body includes an upper surface for contacting the article that is used to develop a dental prosthesis. The analog includes a groove extending inward along a periphery of the main body below the upper surface for receiving a soft modeling material that replicates gingival tissue. Material for forming a soft tissue model flows into the groove to create a corresponding rib in the soft tissue model that allows the soft tissue model to be properly registered on the underlying stone model.

3 Claims, 3 Drawing Sheets

Fig. 4
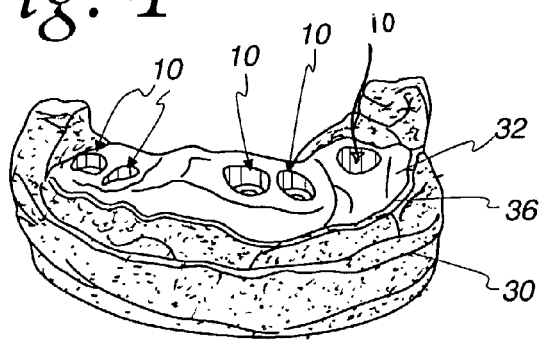
Fig. 5
Fig. 6
(Prior Art)
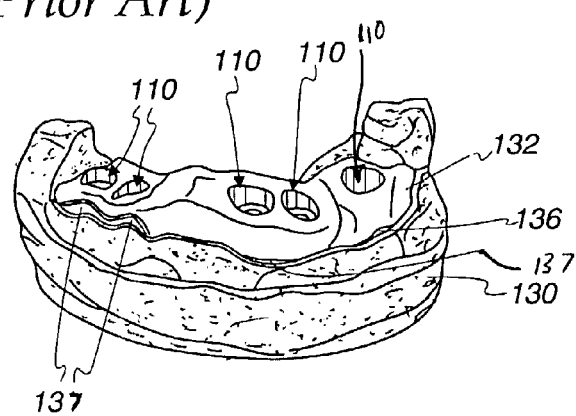
Fig. 7
(Prior Art)
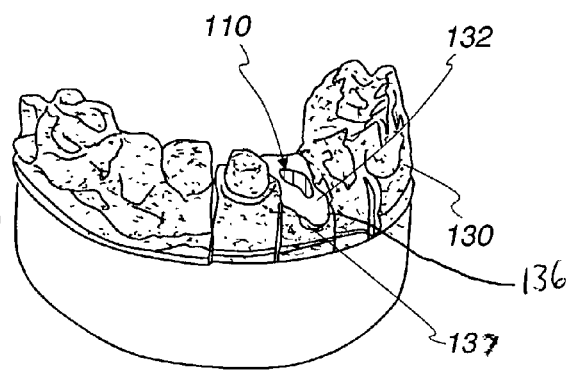

DENTAL IMPLANT ANALOG HAVING RETENTION GROOVE FOR SOFT TISSUE MODELING

FIELD OF THE INVENTION

The present invention relates generally to laboratory components that are useful for making a dental prosthesis and, in particular, to an implant analog that is useful for holding a soft tissue model on a stone model.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, usually a dental implant, is placed in the jawbone for integration. The dental implant generally includes a threaded bore to receive a retaining screw holding mating components therein. During a typical first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. In addition to and separate from the healing abutment, an impression component is fitted onto the exposed end of the implant. This allows an impression of the region of the patient's mouth to be taken so that an artificial tooth is accurately constructed. Preferably, the impression coping has the same gingival dimensions as the healing component so that there is no gap between the impression coping and the wall of the gum tissue defining the aperture. The impression coping may be a "pickup"-type impression coping or a "transfer"-type impression coping, both known in the art.

After these second stage processes, a dental laboratory creates a prosthesis to be permanently secured to the dental implant from the impression that was made. In doing so, the impression coping is located within the impression material and an implant analog is attached to the impression coping. The implant analog replicates (i.e., is "analogous" to) the dental implant that is located within the patient's mouth.

In many instances, the laboratory prefers to have a soft tissue model that replicates the patient's gingival tissue located at the region within the impression that corresponds to the location of the patient's gingival tissue. Thus, the soft tissue model is developed from modeling material placed in the impression around the implant analog. The stone model material is then poured into the impression that includes the soft tissue modeling material and allowed to harden. Once the impression material is removed from the soft tissue model and the stone model, the laboratory can then begin to fashion the final prosthesis on the implant analog.

The laboratory will often want to remove the soft tissue model from the stone model. For example, the laboratory technician may want to visualize the subgingival contours of the dental prosthesis, but cannot do so if the soft tissue model is present. When reinstalling the soft tissue model back onto the stone model, the soft tissue model is simply slid over the implant analog. In prior art implant analogs, however, there is nothing that registers the appropriate location of the soft tissue model on the implant analog or the stone model. Because it is desirable to maintain registration of the soft tissue model on the stone model as accurately as possible, many laboratories will often glue the soft tissue model onto the stone model to hold it in place. When the soft tissue model is removed from the stone model, the glue is removed from the stone model and new glue is added upon reinstalling. This registration problem is accentuated when the laboratory technician is developing a single tooth restoration having very little surface area between the soft tissue model and the stone model for providing registration and between the soft tissue model and the analog.

SUMMARY OF THE INVENTION

The present invention solves the aforementioned problems by providing a novel implant analog for supporting an article that is used to develop a dental prosthesis and a method for using that analog. The analog has a main body for being anchored in a model of a mouth of a patient. The main body includes an upper surface for contacting the article that is used to develop a dental prosthesis. The analog includes a groove extending inwardly along a periphery of the main body below the upper surface for receiving soft modeling material that replicates gingival tissue.

When the implant analog is installed on the impression coping within the impression material, the material for forming the soft tissue model is inserted around the impression coping and the implant analog in the region of this groove so that a rib having a size and shape that generally corresponds to the size and shape of the groove is created in the soft tissue model. Thus, after the stone model and the soft tissue model are developed, the laboratory technician can remove the soft tissue model from the stone model and reinstall the soft tissue model back on the stone model at the precise location. In other words, the groove in the implant analog allows for proper registration of the soft tissue model on the stone model each time the soft tissue model is reinstalled on the stone model.

The groove can be of a variety of shapes and is within about 3 mm of the upper surface of the implant analog. Preferably, the groove is within about 1 mm of the upper surface of the implant analog. The groove is useful on an implant analog that replicates only the dental implant, or on an analog that replicates both the dental implant and the post on which the final prosthesis will be mounted.

The above summary of the present invention is not intended to represent each embodiment, or every aspect of, the present invention. This is the purpose of the figures and the detailed description which follow.

BRIEF DESCRIPTION OF THE DRAWINGS

The foregoing and other advantages of the invention will become apparent upon reading the following detailed description and upon reference to the drawings.

FIGS. 4–5 illustrate the precise interfitting of the soft tissue model on the stone model when an implant analog according to the present invention is used within the stone model.

FIGS. 6–7 illustrate the results of the prior art implant analog where gaps are present at the interface between the soft tissue model and the stone model.

Figure 1A:
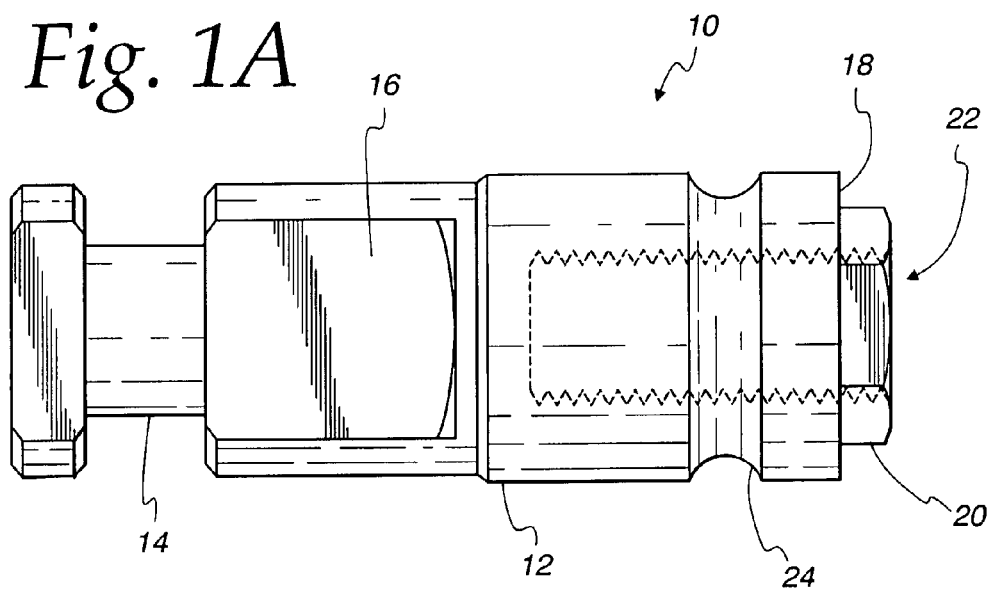
FIGS. 1A–1C illustrate a side view, bottom view, and top view, respectively, of an implant analog according to the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DESCRIPTION OF ILLUSTRATIVE EMBODIMENTS

Figure 1B:
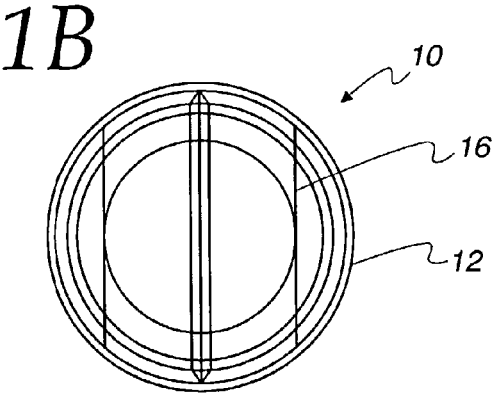
Figure 1C:
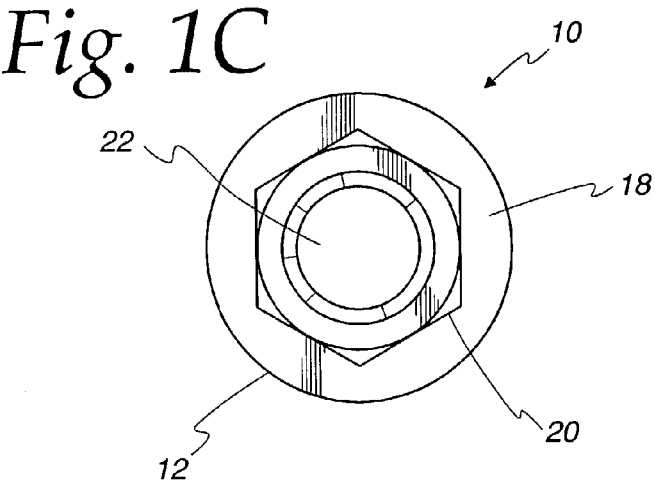

FIGS. 1A–1C illustrate an implant analog 10 that is to be embedded in a stone model that replicates the prevailing conditions of a mouth of a dental patient. The analog 10 includes a main body 12 that has a lower groove 14 and a flat region 16. The flat region 16 resists rotational movement of the implant analog 10 when it is embedded in the stone model. The lower groove 14 prohibits movement of the implant analog 10 in the axial direction when it is embedded in the stone model.

The analog 10 includes an upper surface 18 that supports an article that is used by a laboratory to develop a prosthetic tooth. A fitting 20, shown as a hexagonal boss, is located at the upper surface 18. The fitting 20 could also be a polygonal socket that extends into the upper surface 18. A threaded bore 22 extends into the main body 12 of the implant analog 10 and serves to receive a screw that holds the laboratory article on the upper surface 18 of the analog 10. Unlike implant analogs in the prior art, the analog 10 includes a circumferential groove 24 that is positioned below the upper surface 18. Generally, the groove 24 is located within 3 mm of the upper surface 18, and is preferably within about 1 mm of the upper surface 18.

The upper surface 18, the fitting 20, and the threaded bore 22 are intended to replicate identical features of a dental implant that has been installed into the jawbone of the patient. Accordingly, the implant analog 10 provides features on which the dental prosthesis can be developed by the dental laboratory so that once the final prosthesis is complete, the dental prosthesis will fit in substantially the same manner and orientation on the implant embedded in the jawbone of the patient. While the analog 10 that is illustrated is intended to replicate a dental implant, the present invention covers analogs that are intended to replicate a dental implant and a post coupled to the dental implant, wherein the final dental prosthesis is to reside around the post.

Figure 2:
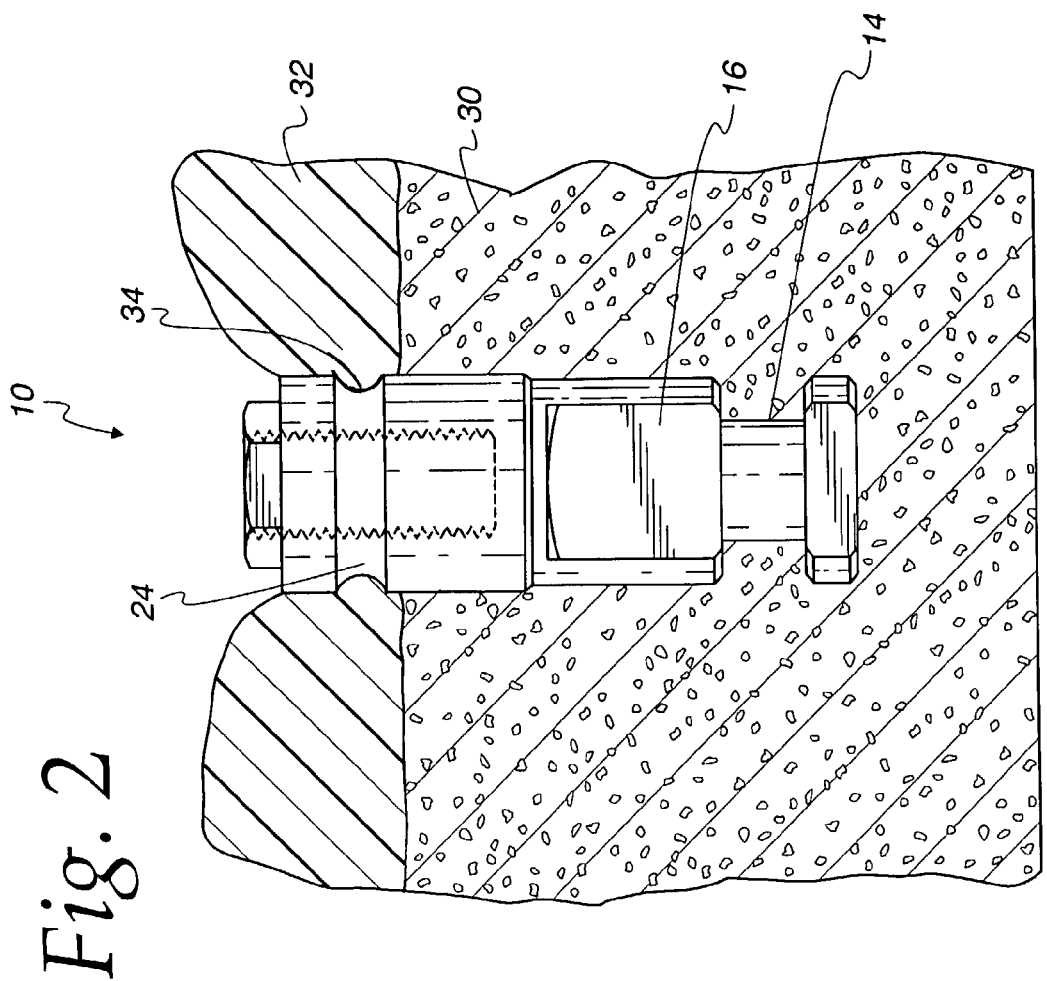
FIG. 2 illustrates the implant analog imbedded within a stone model with a soft tissue model around its upper portion.

FIG. 2 illustrates the usefulness of the groove 24 when the implant analog 10 is embedded in a stone model 30. The stone model 30 is engaging the flat region 16 for resisting rotation of the implant analog 10 within the stone model 30 and the lower groove 14 for resisting the axial movement of the implant analog 10. The groove 24 serves to receive the modeling material that will comprise the soft tissue model 32 replicating the patient's gingiva. Because the modeling material, while it is being applied, moves into the area of the groove 24, the soft tissue model 32 will have a corresponding rib 34. The mating of the groove 24 and the rib 34 is important because the soft tissue model 32 is often removed from the stone model 30 while the laboratory is fabricating the final prosthesis. Accordingly, the mating of the groove 24 and the rib 34 provides the proper registration of the soft tissue model 32 on the stone model 30 leading to a precise interface 36.

While the groove 24 has been shown as having a curvilinear profile when viewed from the side of the implant analog 10, the groove 24 can also be defined by the plurality of surfaces that extend inwardly from the exterior surface of the main body 12. For example, the groove 24 can be defined by two angled surfaces, resulting in a V-shaped groove. Alternatively, the groove 24 can be defined by three surfaces, two of which extend generally horizontal with respect to the axis of the analog 10 and one which extends vertically with respect to the axis of the analog 10, resulting in a rectangular shaped groove. The groove 24 preferably has an axial length that is about 1 mm. The depth of the groove 24 is preferably about 0.5 mm to about 1 mm. With respect to the main body 12, the transverse dimension within the groove 24 is about 60% to about 80% of the transverse dimension of the main body 12. While the illustrated groove 24 extends entirely around a periphery of the main body 12, a groove extending around only a portion of the periphery would also serve the function, as well. Furthermore, the groove may be comprised of a dimple or a series of dimples extending partially or entirely around the periphery of the main body 12. Each of the series of dimples could overlap, or be separated from, adjacent dimples.

The procedure to develop the stone model and the soft tissue model is known to those of skill in the art. First, an impression is taken in a mouth at a site where a dental implant is located. The impression-taking component may be a pickup coping, which is "picked up" for the implant with the modeling material, or a transfer coping, which remains on the implant when the impression material is removed but is "transferred" back into the impression material at a later point. In either case, the impression component is located within the impression material when the models are developed after the impression is removed from the mouth. The implant analog 10 is then attached to the impression component such that it replicates the dental implant at the site where the impression was taken. Thus, the impression component and the attached implant analog are then fixed at a known position relative to the impression material.

A modeling material is added into the impression at a region where the implant analog 10 and impression component are located. A portion of the modeling material enters the groove 24 to develop the rib 34 in the soft tissue modeling material. The modeling material then hardens into a resilient, soft tissue model 32 that includes the rib 34 defined by the portion of the modeling material that entered the groove 24. The material for the stone model is then poured into the impression and replicates the remaining portions of the site, including the adjacent natural teeth and their associated gum tissue. The stone model 30 hardens and the impression material is removed from around the stone model 30 and the soft tissue model 32. The laboratory technician then crafts a core (usually metallic) for the dental prosthesis on the implant analog 10. This crafting often includes the step of removing the soft tissue model 32 from the stone model 30. Reinstalling the soft tissue model 32 onto the stone model 30 is accurately carried out by the rib 34 engaging the groove 24. A tooth replicating material is added to the core to develop the final prosthesis, which is ultimately attached to the dental implant in the patient's mouth.

The soft tissue model 32 can be made of any suitable plastic or rubber-like material having physical properties, such as softness and elasticity, that preferably resemble the physical properties of gingival tissue. Certain silicone-based rubber and plastic materials are suitable, preference being given to those that can be fabricated from a soft flowable state. In use, the soft flowable plastic material is placed in the impression around the impression component and the implant analog 10 to a thickness of about 2 mm to 4 mm. The best results are obtained if different materials are used for the impression material and the soft tissue model 32 to prevent bonding between the soft tissue model 32 and the impression material.

Figure 3:
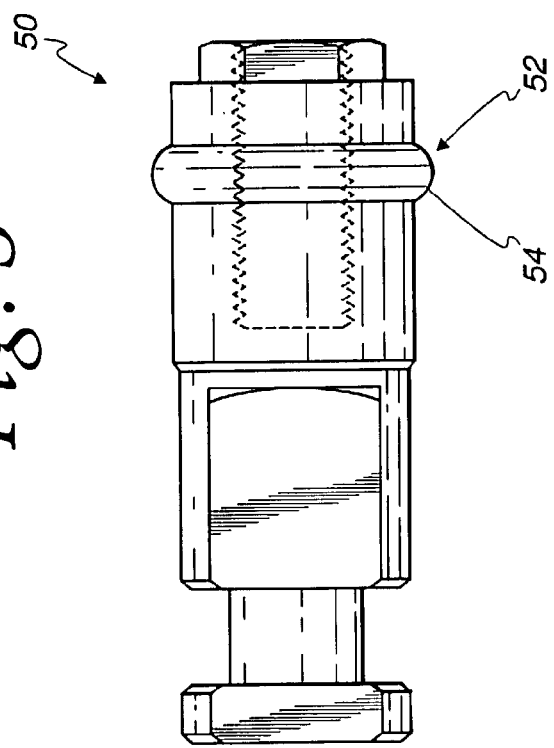
FIG. 3 illustrates an alternative embodiment of the implant analog according to the present invention.

FIG. 3 illustrates an alternative embodiment of the present invention that includes an implant analog 50 having a circumferential rib 52. A circumferential rib 52 extends entirely around the periphery of the main body of the implant analog 50 and defines an underside surface 54. Accordingly, when the material comprising the soft tissue model is applied around the upper region of the implant analog 50, that material will harden with an internal recess that mates with the circumferential rib 52. Again, when the soft tissue model has been placed over the stone model, the mating of the circumferential rib 52 and the recess in the soft tissue model will result in a precise interface between the stone model and the soft tissue model. Thus, while the groove 24 in FIGS. 1 and 2 creates an undercut in the soft tissue model, the underside surface 54 of the circumferential rib 52 also creates an undercut in the soft tissue model that provides for a tactile feedback mechanism for the laboratory technician when placing the soft model over the stone model. This tactile feedback mechanism provides assurance to the laboratory technician that the soft tissue model is registered in the proper position on the stone model such that there are only nominal gaps at the interface between the stone model in the soft tissue model. Consequently, the likelihood that a precise final prosthesis can be developed on the implant analog 10 is increased since the surrounding structures (i.e., the stone model and the soft tissue model) are in a consistent position each time the soft model is reinstalled on the stone model after it has been removed.

FIG. 4 illustrates a stone model 32 that includes five implant analogs 10 according to the present invention. The stone model 32 of FIG. 4 would be used for developing a bridge for a patient that would be supported by five implants in the patient's mouth at locations corresponding to the locations of the five implant analogs 10. The implant analogs 10 provide a snap fit for the soft tissue model 32 such that the interface 36 between the soft tissue model 32 and the stone model 30 is precise each time the soft tissue model 32 is reinstalled on the stone model 30.

FIG. 5 illustrates a stone model 32 that is used to develop a single tooth restoration. Thus, one implant analog 10 is placed within the stone model 30 and the stone model 30 receives the soft tissue model 32 on its upper surface. Again, the interface 36 between the stone model 30 and the soft tissue model 32 has only nominal gaps, at best, such that the soft tissue model 32 is properly interfitted on the stone model 30 due to the registration of the rib 34 in the soft tissue model 32 with the groove 24 on the implant analog 10. The benefits of this invention are more pronounced with respect to the development of a single tooth restoration, since there is only one implant analog to retain the soft tissue model 32 on the stone model 30 and a smaller surface area between the soft tissue model 32 and the stone model 30.

FIGS. 6–7 illustrate the use of prior art analogs 110 lacking a groove or a rib that are placed in a stone model 130 that receives a soft tissue model 132 for a multiple tooth replacement and a single tooth replacement, respectively. As is evident, the interface 136 produced by the prior art implant analogs 110 contains several gaps 137 such that the technician has no assurance that the soft tissue model 132 has been restored to its proper place on the stone model 130. Because of the complicated geometry that defines the interface 136, if the technician were to attempt to push down on one side of the soft tissue model 132 in an attempt to remove a visual gap, it is possible that the force placed on that edge of the soft tissue model 132 would cause another portion of the soft tissue model to rise upwardly and create another gap at the interface 136.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A method of developing a dental prosthesis, comprising:
    taking an impression in a mouth at a site where a dental implant is located;
    removing said impression from said mouth;
    installing an implant analog in said impression at said site where said dental implant was located, said implant analog including a groove;
    adding a modeling material into said impression at a region where said implant analog is located, a portion of said modeling material residing within said groove;
    allowing said modeling material to harden into a resilient, soft tissue model that includes a rib defined by said portion of said modeling material;
    developing a stone model from said impression that replicates said site, said groove of said implant analog being exposed outside of said stone model;
    crafting a core of said dental prosthesis on said implant analog including the steps of removing said soft tissue model from said stone model and accurately reinstalling said soft tissue model onto said stone model with said rib engaging said groove; and
    adding a tooth replicating material to said core.

2. The method of claim 1, wherein said step of developing said stone model includes adding material used for said stone model into said impression onto said resilient, soft tissue model.

3. The method of claim 2, wherein said steps of removing said soft tissue model from and reinstalling said soft tissue model on said stone model includes, respectively, disengaging and engaging said rib and said groove with a tactile feedback.

* * * * *